United States Patent [19]

Grubb et al.

[11] Patent Number: 4,755,380
[45] Date of Patent: Jul. 5, 1988

[54] PEPTIDE FROM AMYLOID A AND ANTISERUM THEREFOR

[75] Inventors: Anders O. Grubb; Lennart W. Ljunggren, both of Lund; Helene K. Hansson, Malmo, all of Sweden

[73] Assignee: Gambro Lumdia AB, Sweden

[21] Appl. No.: 826,551

[22] Filed: Feb. 6, 1986

[30] Foreign Application Priority Data

Feb. 15, 1985 [SE] Sweden ................................. 8500712

[51] Int. Cl.$^4$ ...................... A61K 39/395; C07K 7/06
[52] U.S. Cl. ........................................ 424/85; 530/428
[58] Field of Search ............................... 530/324–328; 424/85

[56] References Cited

PUBLICATIONS

Chemical Abstracts, vol. 93, (1980) 184108r.
Chemical Abstracts, vol. 84, (1976) 146444d.
British Medical Journal, vol. 288: 360–361, (1984).

*Primary Examiner*—John Kight
*Assistant Examiner*—Christina Chan
*Attorney, Agent, or Firm*—Lerner, David, Littenberg, Krumholz & Mentlik

[57] ABSTRACT

Substantially pure peptides containing amino acid residues occurring in amyloid A protein and serum amyloid A protein are disclosed. The peptide compounds may be natural or synthetically derived. It is a characteristic feature of the peptides, regardless of their origin, that the sum of the hydrophilicity values of the respective amino acid residues is greater than or equal to zero. Moreover, specific antisera to these peptides are disclosed.

2 Claims, No Drawings

PEPTIDE FROM AMYLOID A AND ANTISERUM THEREFOR

FIELD OF INVENTION

This invention relates to the field of biochemistry. More specifically, this invention relates to the field of protein chemistry.

BACKGROUND OF THE INVENTION

In many chronic illnesses, such as rheumatoid arthritis, tuberculosis, hepatitis and numerous other infections, there is a strong increase in serum amyloid A protein (SAA) found in serum. Frequently, the 28 C-terminal amino acid residues from serum amyloid A (SAA) are cleaved off and the rest of the protein (named AA) localizes in certain organs of an infected patient. Oftentimes, the earliest organs affected are the kidneys and the heart. The presence of AA in organs causes the organs to cease functioning. The illness caused by such AA poisoning is termed amyloidosis and, if not treated, is fatal.

Because of the fatal course that amyloidosis can steer, early detection and treatment through increased action against the basic infection is imperative. An extant method for the detection of AA or SAA based on the production of antisera is described in Maury et al, 1984, British Medical Journal, 288:360. The method described therein has not gained widespread acceptance because of the substantial difficulty in producing antisera specific for AA of SAA. Moreover, the method has been the subject of some criticism such as that found in Pepys, 1984, British Medical Journal, 288:859.

The instant invention relates to substantially pure peptides derived from the C-terminal end of amyloid A protein. Moreover, the invention discloses antisera specific for AA generally, and SAA specifically, which antisera constitutes a valuable means for the detection and the determination of the concentration of amyloid A protein in the serum and otherwise.

SUMMARY OF THE INVENTION

It is an object of this invention to overcome the difficulty of detecting AA by providing an easy mechanism for the synthesis of antisera which is substantially free of contamination because of the substantially pure peptide from which it is derived.

It is a further object of this invention to prepare a C-terminal AA peptide synthetically and derive an antiserum therefrom.

DETAILED DESCRIPTION

A substantially pure peptide containing at least a portion of 28 C-terminal amino acid residues comprising amyloid A having a hydrophilicity value greater than zero was isolated. The characteristic feature of this peptide is that the sum of the hydrophilicity values of the respective amino acid residues is greater than zero. The term "hydrophilicity value" is used in the common manner of the field and in accordance with the manner described in Hopp et al, 1981, Proc. Natl. Acad. Sci., U.S.A, 78:3824. It is understood that the hydrophilicity value of the peptide may be greater than zero and, in a currently preferred embodiment, at least six.

The number of amino acid residues in the peptide may vary so long as antigenic properties of the peptide remain. It is known, e.g. Lerner, 1982, Nature, 299:592, that synthetic peptides which are to act in an antigenic capacity should have at least six amino acids and, preferably, more than six. The amino acid residues comprising the peptide may vary but must at least partially form a sequence occurring naturally in AA.

Surprisingly, the peptide of this invention can be prepared synthetically. The synthetic version of this peptide has substantially the same properties pertaining to the induction of antisera and solubility as the nonsynthetic AA. This is especially beneficial because it permits slight modifications of the naturally occurring peptide to increase the antigenicity of the antisera. Such modifications may be, by way of example, the addition of substituents to the peptide to increase the antigenicity of the peptide. Examples of such substituents include adjuvants and the like. Among the compounds which could be attached to the synthetic peptides to increase antigenicity are high molecular weight carriers. Synthetic peptide preparations which have been found to function well in accordance with the invention for the preparation of specific antisera to amyloid A include a nonapeptide with the amino acid sequence serine, aspartic acid, alanine, arginine, glutamic acid, asparagine, isoleucine, glutamine and arginine. This nonapeptide was found to especially benefit in increased antigenicity from the addition of high molecular weight carriers.

The antiserum produced by this invention, whether by synthetic means or by isolation of substantially pure peptide, has a wide variety of uses. Among these uses, the antiserum can be used for detection of AA in tissue specimens. Furthermore, the antiserum is useful for the determination of the concentration of SAA in blood.

EXAMPLE

A synthetic nonapeptide analog of amyloid A protein was synthesized. The nonapeptide comprised the amino acid sequence serine, aspartic acid, alanine, arginine, glutamic acid, asparagine, isoleucine, glutamine, and arginine. The nonapeptide was coupled with a high molecular weight carrier and injected two times at three week intervals into five rabbits in accordance with conventional technique. All the rabbits produced antisera which reacted specifically with SAA. This was confirmed using immunohistochemical techniques and immunoblot techniques of known type. Production of antisera continued without loss of titer during six weeks without renewed injections of the nonapeptide and carrier complex. These results indicate that the antiserum production may be regarded as stable.

What is claimed is:

1. A synthetic amyloid A peptide consisting of the amino acid sequence serine, aspartic acid, alanine, arginine, glutamic acid, asparagine, isoleucine, glutamine, and arginine.

2. An antisera specific to amyloid A protein prepared from a nonapeptide consisting of the amino acid sequence serine, aspartic acid, alanine, arginine, glutamic acid, asparagine, isoleucine, glutamine, and arginine.

* * * * *

UNITED STATES PATENT AND TRADEMARK OFFICE
CERTIFICATE OF CORRECTION

PATENT NO. : 4,755,380

DATED : July 5, 1988

INVENTOR(S) : Grubb et al.

It is certified that error appears in the above-identified patent and that said Letters Patent is hereby corrected as shown below:

Title page:

In the identification of the assignee, "Gambro Lumdia AB" should read --Gambro Lundia AB--.

Signed and Sealed this

Twenty-ninth Day of November, 1988

Attest:

DONALD J. QUIGG

Attesting Officer

Commissioner of Patents and Trademarks